United States Patent [19]

Jeffers et al.

[11] Patent Number: 5,055,694
[45] Date of Patent: Oct. 8, 1991

[54] METHOD AND APPARATUS FOR MONITORING AND MEASURING THE CONCENTRATION OF ION EXCHANGE RESIN PARTICLES IN WATER

[75] Inventors: Larry A. Jeffers; Jack K. Schmotzer, both of Alliance; Charles C. Stauffer, Beloit, all of Ohio

[73] Assignee: The Babcock & Wilcox Company, New Orleans, La.

[21] Appl. No.: 931,972

[22] Filed: Nov. 24, 1986

Related U.S. Application Data

[63] Continuation of Ser. No. 666,718, Oct. 31, 1984, abandoned.

[51] Int. Cl.$^5$ .................................. G01N 21/64
[52] U.S. Cl. ........................... 250/458.1; 250/461.1; 356/318
[58] Field of Search .................. 250/461.1, 373, 461.2, 250/301, 458.1, 459.1, 365; 356/318, 417

[56] References Cited

U.S. PATENT DOCUMENTS

| | | | |
|---|---|---|---|
| 2,663,801 | 12/1953 | Slavin et al. | 250/461.1 |
| 3,510,648 | 5/1970 | Leger, Jr. | 250/301 |
| 3,906,226 | 9/1975 | Okabe et al. | 250/373 |
| 4,055,768 | 10/1977 | Bromberg | 250/461.2 |
| 4,108,604 | 8/1978 | Heller | 422/68 |
| 4,203,670 | 5/1980 | Bromberg | 356/318 |
| 4,516,856 | 5/1985 | Popelka | 250/461.1 |
| 4,553,034 | 11/1985 | Byers et al. | 250/458.1 |
| 4,599,512 | 7/1986 | Bushaw | 356/318 |

OTHER PUBLICATIONS

Lipson, "Lasers in Fluorescence Spectroscopy", Laser Focus, 6(9), Sep. 1970, pp. 37–38.
Harrington, et al., "New Type of Spectrofluorometer with Tunable Laser Source and Unique Optical System", Anal. Chem., 47(2), Feb. 1975, pp. 271–276.

*Primary Examiner*—Carolyn E. Fields
*Attorney, Agent, or Firm*—Robert J. Edwards

[57] ABSTRACT

A method and apparatus for monitoring and measuring the level of ion exchange resin fragments in very pure water employs a laser light source to illuminate a water sample causing the resin fragments to fluoresce. This light of fluorescence is focused, filtered, and detected by a photodetector, whose electrical signal output is amplified and processed to provide an output related to the concentration of ion exchange resin fragments in the water. Separate calculations or a computer within the apparatus itself produce a measure of the concentration of the resin fragments in the sample. The apparatus and method are useful for maintaining purity of water in boilers employing condensate polisher systems, for example.

1 Claim, 5 Drawing Sheets

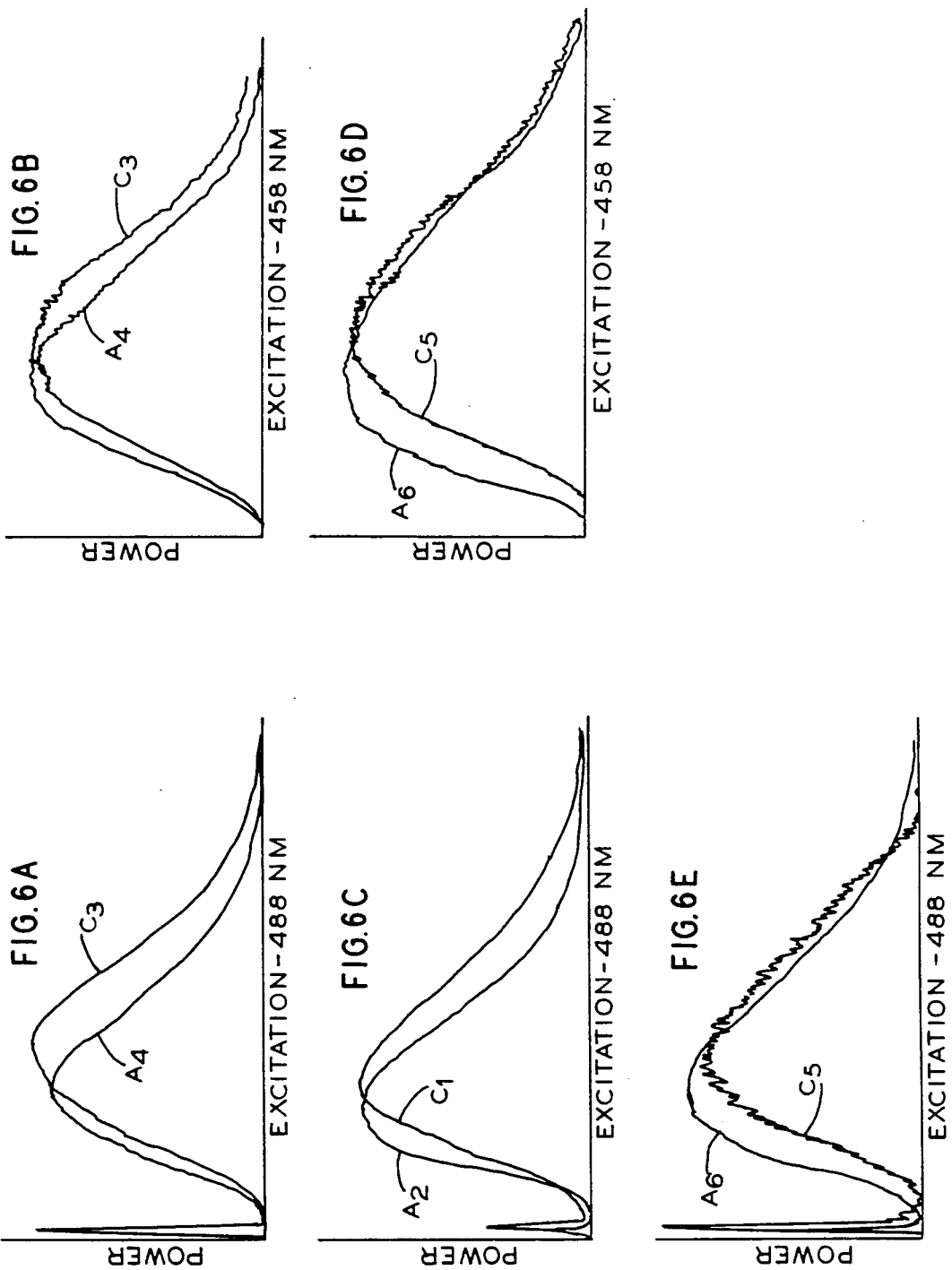

METHOD AND APPARATUS FOR MONITORING AND MEASURING THE CONCENTRATION OF ION EXCHANGE RESIN PARTICLES IN WATER

This application is a continuation of application Ser. No. 06/666,718 filed Oct. 31, 1984, now abandoned.

BACKGROUND OF THE INVENTION

1. Field of the Invention

The present invention is directed to a method and apparatus for detecting the presence of ion exchange resins in a fluid and measuring their concentration. More particularly, the present invention is directed to a test device using a laser light to cause the resin fragments to fluoresce and using their fluorescence to measure the concentration of resin in relatively pure water.

2. The Prior Art

Many industrial and commercial systems require extremely pure water. For example, the art of manufacturing integrated circuits and microprocessors requires that silicon wafers be carefully and thoroughly washed with very pure water between etchings and other manufacturing steps. More particularly, in electrical power generation, boiler feedwater must be very pure or minerals and salts in the water will be deposited throughout the system, reducing its efficiency and shortening its life. In these and other applications, the water used is often treated with ion exchange resins in resin beds to remove impurities. Make-up demineralizers and condensate polisher systems, which are used to purify feedwater, however, leak ion exchange resin fragments into the condensate and feedwater systems during operation. These ion exchange resin fragments are a potential source of impurities such as sulfur, organic chemicals and so forth, and these resins can readily decompose into quite corrosive and reactive organic acids in the boiler system, causing increased corrosion.

In a power plant system, condensate from the turbine is collected in a condenser having a hot well before being pumped back into the system. From the hot well it may be pumped through ion exchange resin beds to remove particulate matter and soluble matter that were introduced from the system or with the makeup water. Leakage of resin fragments occurs during steady state operation and increases substantially during flow transients. For example, when a new bed is put into use increased agitation results in greater leakage of resin into the system. The quantity of leakage varies according to operational variables of the particular system. In a boiler, there are two practical methods of controlling the level of resin contamination in the boiler water. They are generally used together. First, the rate of leakage can be related to the specific details of operation of the boiler and the resin beds. By manipulating these variables over time through gained experience, the level of leakage can be reduced. Second, the blowdown of the system can be increased to remove contaminants faster. Most contaminants are not soluble in steam, so they collect in the water in the boiler. Conventionally, a portion of this water, for example, 0.1%, is continuously removed from the boiler and discarded. Were this not done, the boiler would eventually become filled with sludge. Effective use of both of these methods requires that the level of contaminants is known. The present invention focuses on the level of ion exchange resin fragments in the water, rather than other contaminants.

The prior art includes two methods of measuring the level of ion exchange resin fragments in the boiler water. In the first method, a membrane filter collects resin fragments from a sample of water. The filter is transferred to a specially modified centrifuge tube where an organic solvent dissolves the membrane filter. The filtrate is spun in the centrifuge tube which drives particulate matter into the precision bore stem of the centrifuge tube. The column height of the material is measured, permitting calculation of the volume of the material. The same analysis is preformed on a resin standard of known weight to obtain an apparent density. The weight of the sample is estimated therefrom. This method is extremely labor intensive. It requires filtering a large sample of water on the order of tens or hundreds of liters because the test checks for concentrations in parts per billion. The test is extremely time consuming, requiring several hours of analysis time, leading to stale information. The method also requires special laboratory equipment not commonly available at power stations or other boiler installations. Finally, occasionally interference from other particles, such as iron oxides and colloidal silica and from the membrane filter itself, is encountered.

A second method involves treating the membrane filter with cationic and anionic radiotracers and taking a reading from the sample on a gamma spectrometer. These readings are then compared with readings taken from known standards and the amount of resin fragments is estimated. This method is also very labor intensive and requires sampling tens or hundreds of liters of water. It also takes several hours to perform, reducing the usefulness of the then stale information. The method requires special laboratory equipment not commonly available at power stations or other boiler installations.

These substantial shortcomings in the methods of the prior art have resulted in only sporadic use of condensate polisher systems in boilers. Consequently, a clear need exists for a method and apparatus for conveniently, quickly and inexpensively monitoring and measuring the level of resin fragments in water.

SUMMARY OF THE INVENTION

Accordingly, it is a primary object of the invention to provide a test apparatus overcoming these and other deficiencies of the prior art.

More particularly, it is an object of the present invention to provide a method of monitoring and measuring the concentration of ion exchange resin particles that permits continuous real time monitoring and measuring.

It is a further object of the present invention to provide a method for monitoring and measuring the concentration of resin fragments that is less labor intensive than the prior art.

It is a further object of the present invention to provide a method of monitoring and measuring the concentration of resin fragments that is not subject to interference from non-resin particles and consequently false readings.

It is a further object of the present invention to provide an apparatus that will carry out the inventive method in the presence of many commercially available ion exchange resins.

It is a further object of the present invention to provide an apparatus for carrying out the inventive method that is relatively inexpensive and affordable to potential users.

It is a further object of the present invention to provide an apparatus for carrying out the inventive method that is relatively easy to use.

Accordingly, the present invention provides an excitation source, which may be a laser or other light source, whose light is directed into a sampling cell where it impinges on ion exchange resin fragments suspended in the flowing stream. These resin particles or fragments fluoresce. The light of fluorescence of the resin fragments exits the sampling cell where it is focused by a lens, passed through a wavelength filter and impinges on a photodetector. The wavelength filter filters out all light including any scattered laser light, except the characteristic wavelengths emitted by the particular resin fragments within the system. The signal from the photodetector is transmitted to the electronics for processing. The monitor is calibrated using known resin standard samples containing known amounts and types of ion exchange resins.

Most ion exchange resins used in condensate polisher systems are sensitive to light ranging from ultraviolet to blue-green in the spectrum and fluoresce when exposed to it. Most aromatic hydrocarbons fluoresce when exposed to light ranging from ultraviolet to blue-green, but most inorganic compounds do not. This fact increases the accuracy and utility of the present invention because inorganic contaminants commonly found in boilers do not cause spurious readings, a serious problem with some prior art methods. Fluorescent materials fluoresce with characteristic wavelengths that are a part of their physical properties. The wavelength of the impinging light may determine whether or not the substance fluoresces, but the substance always returns its fluoresced light at specific wavelengths. The power of the impinging light source only affects the strength of the return signal, that is, the fluoresced signal, not whether the compound will fluoresce at all. These facts permit the method of the present invention to distinguish one type of resin or ion from the other, making the method very useful for distinguishing between anion and cation resin fragments, which can be important because cation resin fragments are more deleterious to the boiler components.

BRIEF DESCRIPTION OF THE DRAWINGS

FIGS. 6A–E are graphic representations of the different spectra emitted by anion and cation resins from different commonly commercially available ion exchange resins listed in Table 1.

DETAILED DESCRIPTIONS OF THE PREFERRED EMBODIMENT

Figure 1:
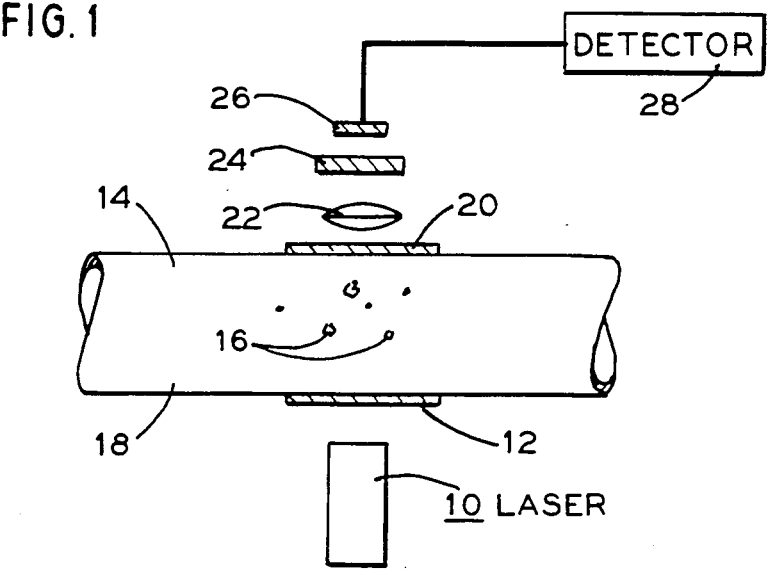
FIG. 1 is a schematic of an apparatus according to the present invention.

As illustrated in FIG. 1, the apparatus for carrying out the invention comprises laser 10, whose light is directed through transparent window 12 into sample fluid 14 where it impinges on particles 16 inside sampling cell 18. Some particles 16 are resin fragments and will fluoresce. Other particles are inorganic compounds and usually will not fluoresce. Some light of fluorescence is transmitted through monitoring window 20, then collected and focused by lens 22, which directs the fluorescent light through wavelength filter 24, which filters out all irrelevant wavelengths, including laser light not absorbed by resin fragments. Then the filtered light falls on photodetector 26, producing an electric current proportional to the intensity of the filtered light falling on the photodetector. From photodetector 26 this current is transmitted to standard electronics 28, which convert the signal into an output signal related to the concentration of resin fragments in the sample. The output of standard electronics 28 may be in any convenient form, that is, a graph or chart, columns of numbers in computer memory or hard copy output, as desired.

It has been found that a preferred laser is a helium-cadmium laser (He-Cd laser), which produces light at about either 325 nanometers in wavelength (nm) (ultraviolet) or 442 nm (blue) is a standard instrument that is relatively reliable, has an expected life of about 4,000 hours and is relatively inexpensive. The tests described below in detail illustrate that an argon laser which can produce light at about 458 nm or 488 nm can also be used to excite fluorescence in the resin fragments of eight of the most commonly commercially available ion exchange resins used in condensate polisher systems. Either a continuous output laser or a pulsed output laser can be used in the monitor. Either permits constant real time monitoring of actual temporal concentration for the ion exchange resin. An integration time of one second is more than sufficient to monitor the sample adequately. If the feedwater is homogeneous then a one second integration period is sufficient to measure adequately the concentration of resin particles in the water. The procedure according to the present invention can provide test results accurate to within about $\pm 5\%$, which is superior to the prior art methods ($\pm 20\%$).

The laser is a preferred light source because it can be precisely focused to a beam of known size permitting precise calculation of the actual volume of sample fluid being monitored. Using a well known series of equations and straightforward empirical studies, it has been found that a laser power of 15 milliwatts (mW) at a wavelength of 458 nm illuminating the particle of approximately 50 micrometers leads to a fluorescent power of about 5 times $10^{-8}$ watt through a solid angle of pi/16. This permits the estimated sample calculation that fluorescent power expected for passage of a single particle through the sample volume is 1.5 times $10^{-8}$ times the diameter in micrometers of the particle times the power in watts incident on the particle. This is true as long as the particle size is greater than the diameter of the sampling beam. If the particle diameter is less than the sampling beam diameter, the fluorescent signal power is predicted to be smaller by the factor of the square of the ratio of the particle diameter to the sample beam diameter. Using a silicon photodiode detector the minimum detectable signal power is approximately $10^{-13}$ watts, and using a photomultiplier detector the minimum detectable power is approximately $10^{-16}$ watts. This leads to the finding that the corresponding minimum detectable particle size is about 0.8 micrometers and about 0.08 micrometers, respectively assuming a beam diameter of 30 microns and an incident power of 10 mw. These conservative values are based on measured fluorescent effciencies in a laser wavelength of 458 nm (argon laser). With a helium-cadmium laser operating at 442 nm or 325 nm, the efficiency would be expected to be higher due to a stronger absorption coefficient at these frequencies in the resin fragments. The size limit can be further reduced by focusing the laser light to a smaller spot size. The tradeoff is that as the sample volume decreases, it takes a longer integration period to detect a given particle concentration.

Sampling cell 18 may be of any convenient material capable of withstanding moderate temperature and pressure, such as steel, and inlet window 12 and monitoring window 20 are conventionally made of glass and sealed conventionally within openings in sampling cell 18. Only one window is actually required, since back-scattered fluorescence can be measured as easily and effectively as forward scattered fluorescence. Two windows are used here only to simplify the drawing and conceptual flow of light through the system. It is also feasible to build a transparent sampling cell 18.

Lens 22 focuses the light that fluoresces from particles 16 and passes it through wavelength filter 24, which filters out all light except the characteristic wavelength emitted by the resin fragments. Naturally, the type of filter may be affected by the type of ion exchange resin in the system, although a Corning 3-71 filter has been found to be effective in monitoring intensity of fluoresced light from the eight ion exchange resins tested. The filter completely absorbs all the scattered laser light. Fluorescent light transmitted by wavelength filter 24 impinges on photodetector 26, which may be a conventional silicon photodiode detector, a photomultiplier detector, or other convenient photodetector. The types and sensitivities of available photodetectors for this purpose are well known to those skilled in the art. The electrical signal from the photodetector is transmitted to conventional electronics 28, well known to those skilled in the art, which provides a record and a reading of the concentration of resin fragments in the sample. In a preferred embodiment, sample fluid flows continuously through sampling cell 18.

Table 1 reproduced below lists the nine different samples tested for detection by the monitor and to quantify the variability in fluorescence among different resins. Sample resins are listed according to their commercial names because they usually are purchased on the basis of their commercial brand name and their exact composition is a trade secret, so that their chemical composition cannot be specified herein with any great accuracy. The eight active resins are all extensively used in ion exchange beds and particularly in condensate polisher systems. The sample numbers given in Table 1 below are those reproduced in the figures of ion exchange resin fluorescent emissions spectra in FIGS. 2-6. These figures illustrate that the fluorescent emissions spectra can be used to detect the presence of resin fragments.

Sample 7 consisted of inert beads, which did not fluoresce under the test light frequencies used. It is believed, however, that these inert beads, being organic chemical compounds, may fluoresce when exposed to a yet untried frequency. It is not known how much this present shortcoming may reduce the utility of the monitor. Inert beads are not chemically reactive in ion exchange resin beds. Their purpose is to permit a better separation of cation resins and anion resins during regeneration of the resin beds, which they facilitate by floating between the anion resins and cation resins when these are stratified prior to regeneration. Because the inert beads are not chemically reactive in the resin bed, they do not carry deleterious chemicals with them as cation resins and anion resins do. Therefore inert beads themselves, unlike used anion resins and cation resins, do not cause harmful effects inside the power generation plant. The inert beads tend to decompose into other compounds when exposed to high temperature and pressure. The exact nature of these compounds and their effect on power generation systems, however, is not known. The present invention nonetheless represents a significant advance in the state-of-the-art and it is clear that cation resins and anion resins that escape into the boiler system are more deleterious than are escaped inert resins.

TABLE 1

| Sample # | Identification | Morphology | Appearance |
|---|---|---|---|
| 1 | Cation Dowex HCR-W | 500 micrometer spheres | Transparent amber/yellow |
| 2 | Anion Dowex HCW-W | 500 micrometer spheres | Transparent amber/yellow |
| 3 | Cation Dowex HCR-W | 500 micrometer spheres | Transparent amber/yellow |
| 4 | Anion Dowex SBR-P | 500 micrometer spheres | Transparent pale amber |
| 5 | Cation Rohm & Haas Amberlite 252 | 1000 micrometer spheres | Opaque-coal black |
| 6 | Anion Rohm & Haas IRA 900 | 500 micrometer spheres | Opaque-light tan |
| 7 | Inert Rohm & Haas Ambersap 359 | 500 micrometer spheres | Transparent-colorless |
| 8 | Mixed Powder, Epicor SWCA Premixed Cation/Anion | 25 micrometer powder | Tan |
| 9 | Mixed Powder- Epicor PD-2 Cation Epicor PD-1 Anion | 25 micrometer powder | Whitish |

Figure 2:
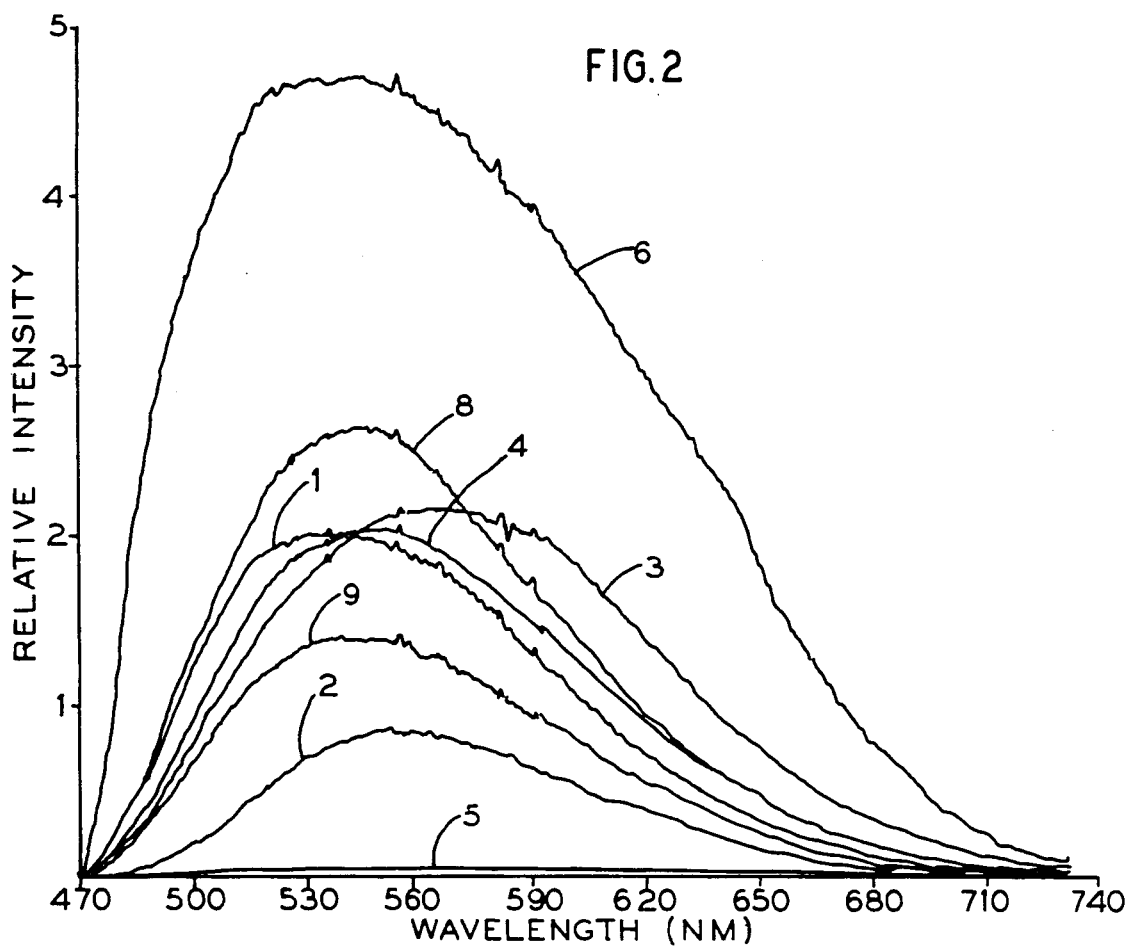
FIG. 2 is a graphic representation of the fluorescent spectra of eight commonly available commercial ion exchange resins produced by exposure to laser light of 458 nm.
Figure 3:
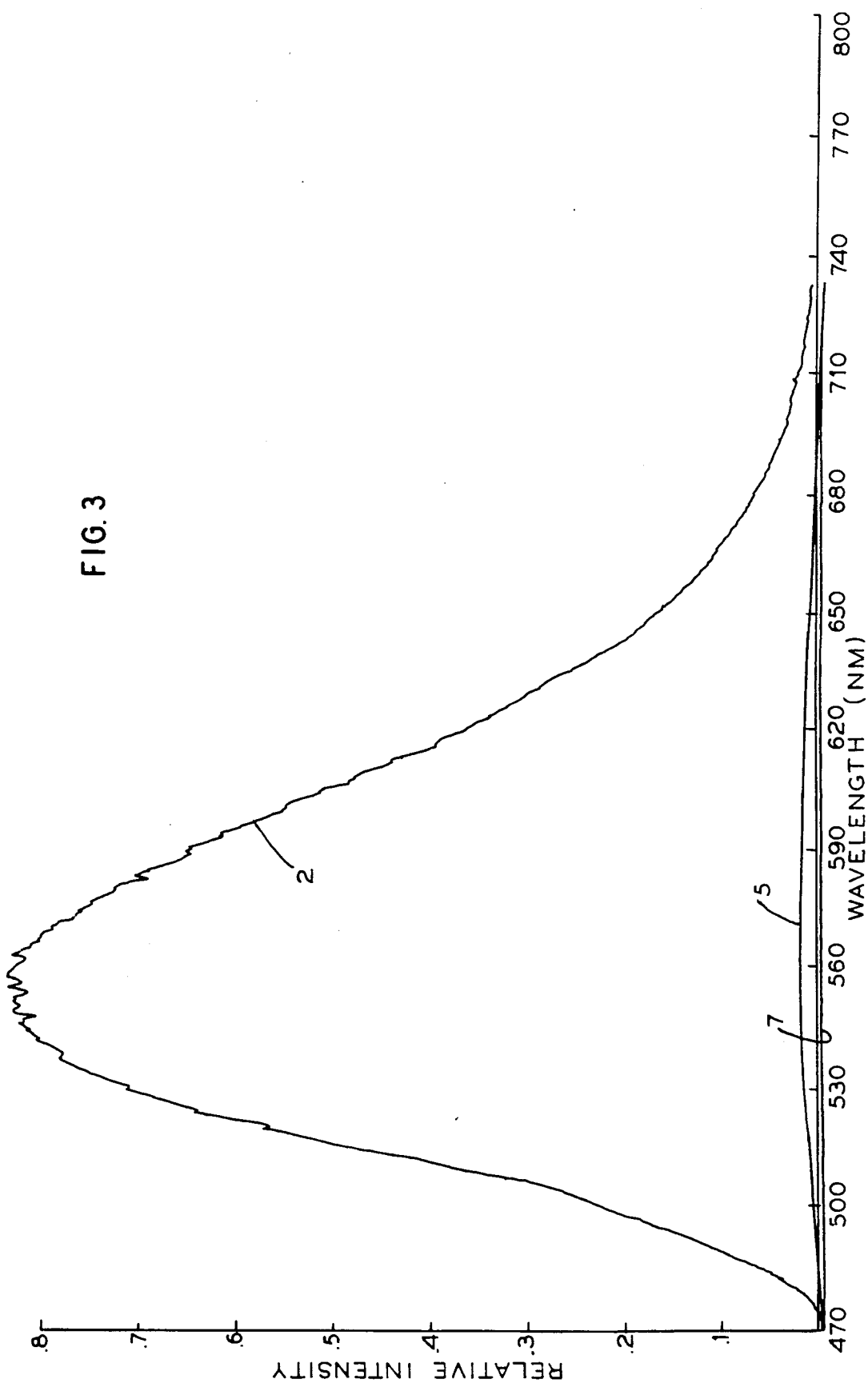
FIG. 3 is a graphic representation of the fluorescent emission spectra of three samples of commonly available ion exchange resins for excitation at about 458 nm.
Figure 4:
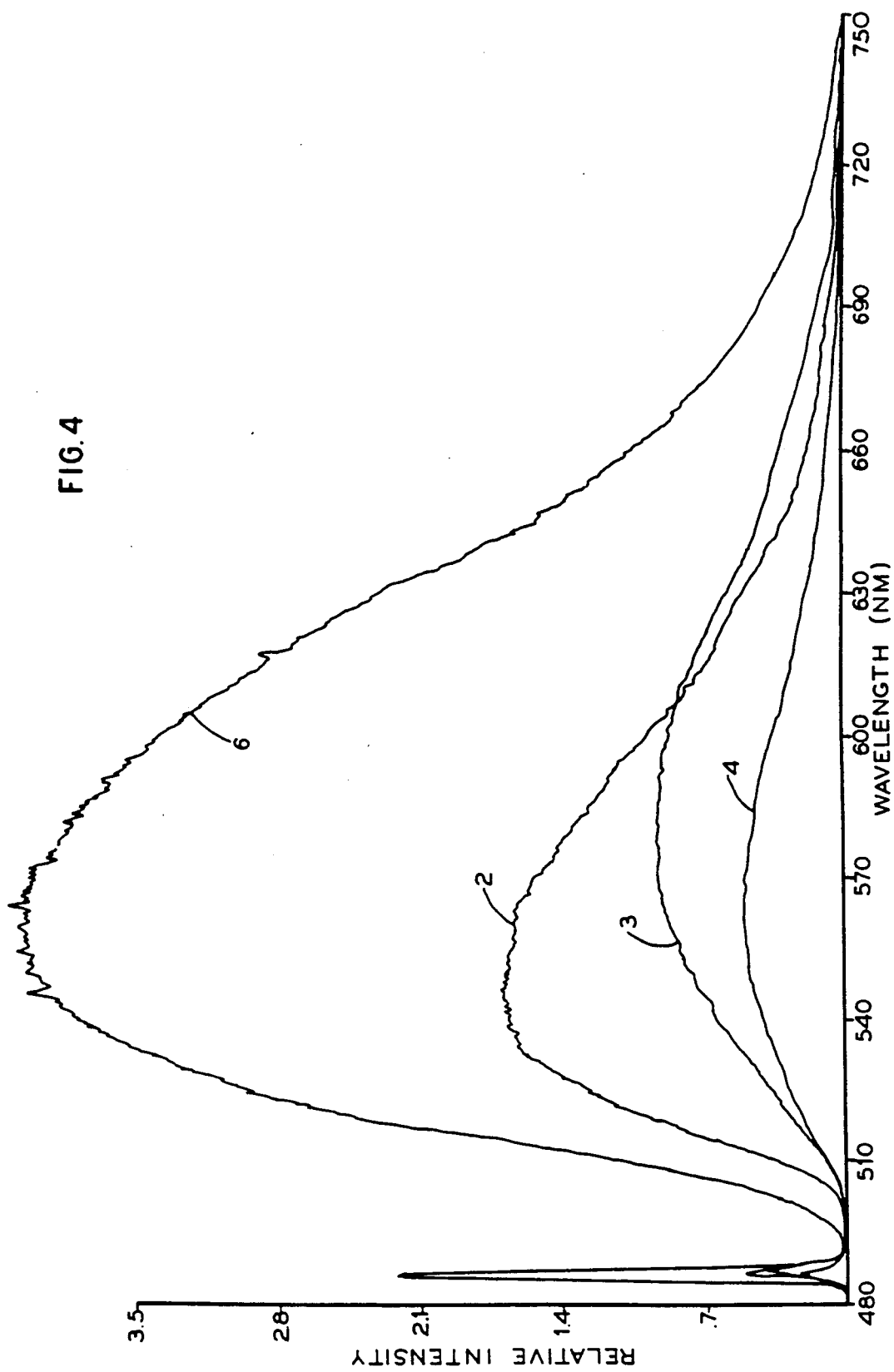
FIG. 4 is a graphic representation of the fluorescent emission spectra of four samples of commonly available ion exchange resins for excitation at about 488 nm.
Figure 5:
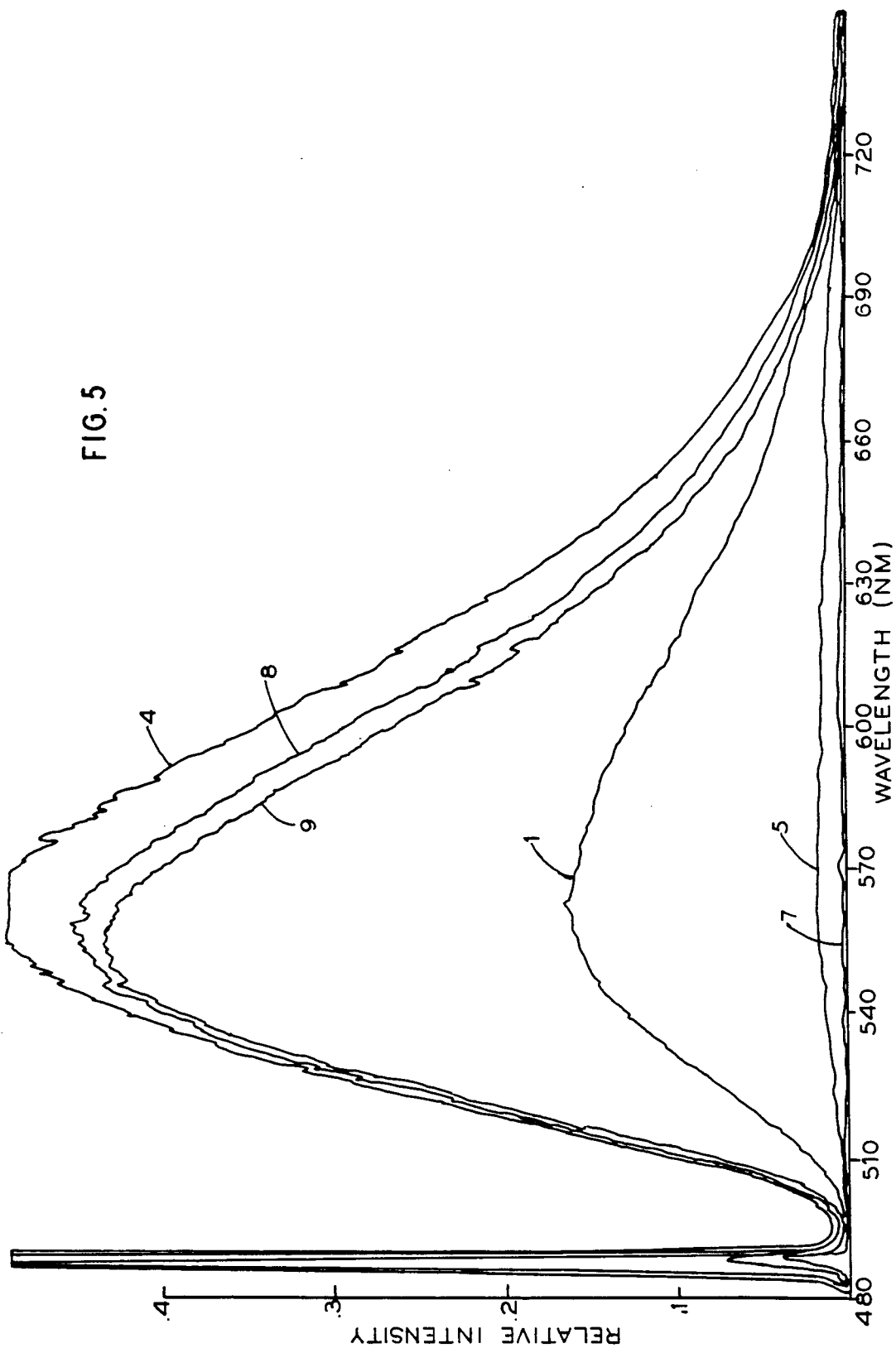
FIG. 5 is a graphic representation of the fluorescent emission spectra of six samples of commonly available ion exchange resins for excitation at about 488 nm.

FIG. 2 illustrates fluorescent emissions spectra for Samples 1, 2, 3, 4, 5, 6, 8 and 9 for excitation at approximately 458 nm. Most samples fluoresce at a maximum around 560 nm. FIGS. 3-5 illustrate the further fluorescent emissions spectra of different samples with greater sensitivity and detail. FIGS. 6A-E illustrate the different emission spectra produced by anion, A, and cation, C, resins. All curves have been normalized to approximately the same height to better illustrate changes in shape of the relative spectra. The peak intensity of the fluorescent spectrum occurs at different wavelengths in each case and particularly when comparing anions and cations. In particular, the peak of fluorescence intensity in the anion occurs at a lower wavelength than for the cation, making it possible to distinguish between the presence of anion resins and cation resins in the sample. Because the fluorescence of resins differs considerably, the minimum detectable fragment size varies by as much as a factor of ten, depending on the particular resin used. In each case, however, submicron sized resin fragments can be detected. The monitor is applicable to a wide range of different resins, including all eight active samples illustrated above. The apparatus according to the present invention is capable of detecting parts per billion levels of resin fragments in very pure water.

While the invention has been described with respect to a particular preferred embodiment, it is clear that changes and additions may occur to those skilled in the art upon review of this patent and that the scope of the invention should be measured from the claims that follow rather than the description of the preferred embodiment.

We claim:

1. An apparatus for detecting the actual temporal concentration of a known type of ion exchange resin in very pure water from a location external to the water, comprising:

(a) a sampling cell for receiving a stream of continuously flowing water to be tested, said cell having two monitoring windows therein positioned so that the stream passes across said windows;

(b) a laser adjacent said sampling cell and positioned for transmitting a laser light beam of known diameter from outside said cell directly into said sampling cell through one of said monitoring windows, said laser light beam being at a wavelength predetermined to cause the resin to fluoresce at a characteristic wavelength and for illuminating a well defined actual volume of water in the sampling cell which can be precisely calculated, the laser being selected to transmit a laser light beam having a diameter of 30 microns and an incident power of 10 mW, so that particle sizes of the ion exchange resin of about 0.08 micrometers are detected;

(c) a lens adjacent and outside of said sampling cell and positioned adjacent the other one of said monitoring windows for focusing incident light from said sampling cell, which incident light includes scattered laser light and light produced by fluorescence of the resin which leaves said sampling cell through the other one of said monitoring windows;

(d) a light filter adjacent said lens for passing only wavelengths of fluoresced light characteristic of the resin to be detected;

(e) a photomultiplier detector positioned to receive light of said characteristic wavelengths that passes through said filter and to convert the light into an electric signal; and (f) means for using the electric signal to produce a desired output which is usable with the precisely calculated actual volume of the water illuminated by the laser light beam to determine an actual temporal concentration of the ion exchange resin in water passing across said windows.

* * * * *